Figure 1:
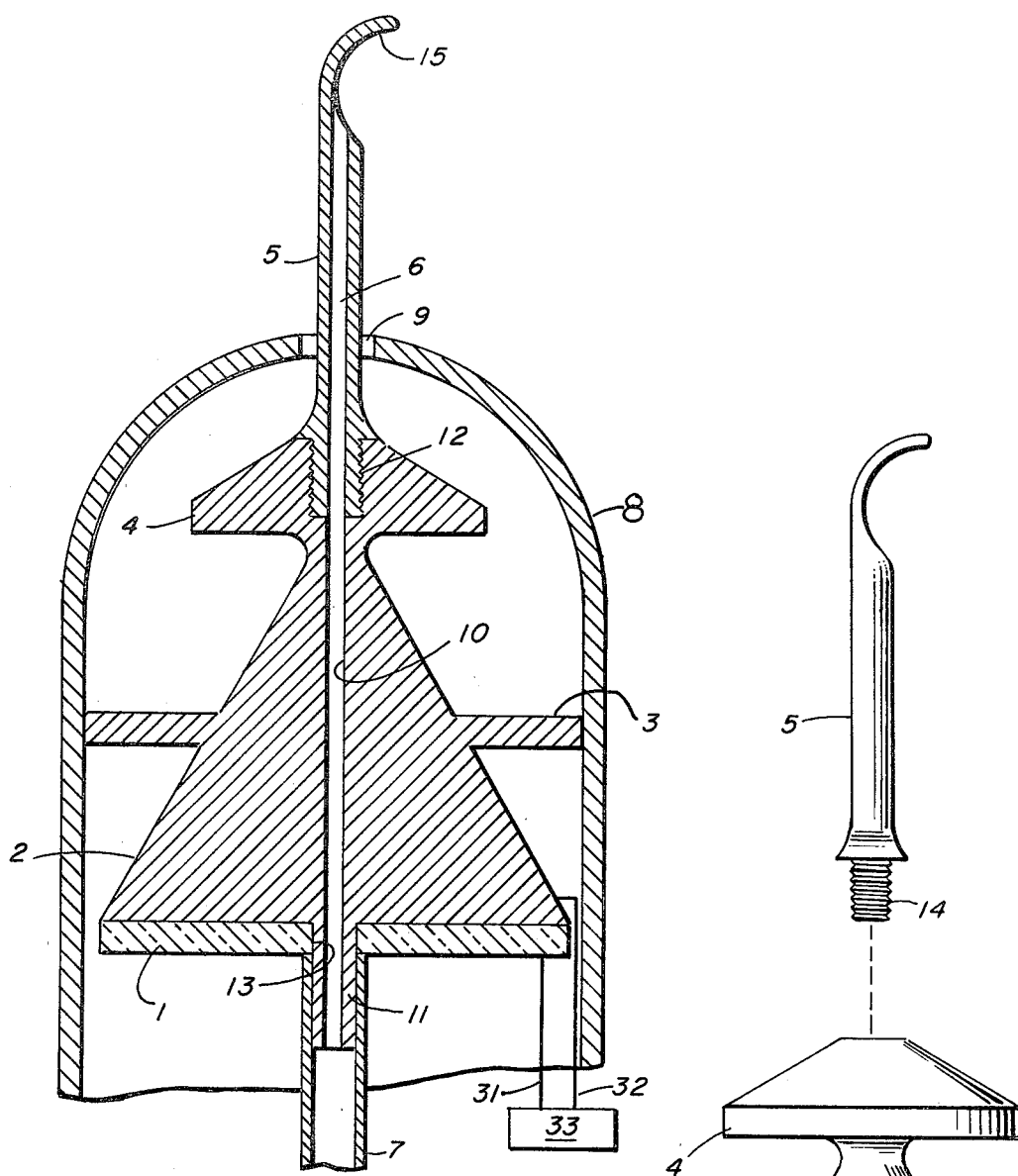

United States Patent [19]

Lustig

[11] 4,332,558

[45] Jun. 1, 1982

[54] DENTAL SCALING APPARATUS

[76] Inventor: Leopold P. Lustig, 304 Greenwood St., Newton Centre, Mass. 02159

[21] Appl. No.: 151,630

[22] Filed: May 20, 1980

[51] Int. Cl.³ ............................................... A61C 1/07
[52] U.S. Cl. ..................................... 433/86; 433/119; 51/59 SS
[58] Field of Search ......................... 433/86, 119, 118; 128/24; 51/59 SS

[56] References Cited

U.S. PATENT DOCUMENTS

| | | | |
|---|---|---|---|
| Re. 25,033 | 8/1961 | Balamuth et al. | 433/119 |
| 2,774,193 | 12/1956 | Thatcher et al. | 433/119 |
| 2,804,724 | 9/1957 | Thatcher | 51/59 SS |
| 3,368,280 | 2/1968 | Friedman | 433/86 |
| 3,589,363 | 6/1971 | Banko et al. | 128/24 A |
| 3,608,648 | 9/1971 | Dibble, Jr. | 51/59 SS |
| 3,654,502 | 4/1972 | Carmona et al. | 433/86 |
| 3,693,613 | 9/1972 | Kelman | 128/24 A |
| 3,703,037 | 11/1972 | Robinson | 433/86 |

FOREIGN PATENT DOCUMENTS

| | | | |
|---|---|---|---|
| 2032433 | 1/1972 | Fed. Rep. of Germany | 433/119 |
| 2107526 | 8/1972 | Fed. Rep. of Germany | 433/86 |

*Primary Examiner*—Gene Mancene
*Assistant Examiner*—John J. Wilson
*Attorney, Agent, or Firm*—Alfred H. Rosen

[57] ABSTRACT

An ultrasonically vibrated dental scaling apparatus with liquid feed through the scaling tool, in which the tool is mounted to one end of a tuned coupler having a piezoelectric transducer at the other end, and the liquid feed is through the member which drives the tool.

5 Claims, 4 Drawing Figures

DENTAL SCALING APPARATUS

BACKGROUND OF THE INVENTION

In the care of teeth it is important to remove accumulated deposits, called "calculus". This is now well known, and public education programs are carried out by both the dental profession and public health authorities with the intention that each person will take proper care of his or her teeth. Yet, in spite of all such efforts vast numbers of people do not take proper care of their teeth, with the result that dentists and dental hygienists must frequently remove calculus from the teeth of their patients before other treatments can be performed. This invention relates to an improved electromechanical apparatus for scaling teeth in a safe, gentle and effective way.

Teeth can be scaled by hand, using hand-scrapers made especially for the purpose, but that is a tiring and time-consuming process. To alleviate it, electromechanical scalers which vibrate mechanically at a high frequency, preferably above audible (ie: "ultrasonic"), have been introduced. Typically, prior electromechanical vibrating scalers are elongated tools that are driven into longitudinal vibration by an electromechanical transducer, to the end that one end of the tool when applied to the surface of a tooth will chip away the calculus deposited on that surface. These tools are effective, not only to remove calculus but, unfortunately, sometimes also to damage the tooth or the tissues surrounding it.

GENERAL NATURE OF THE INVENTION

Figure 1A:
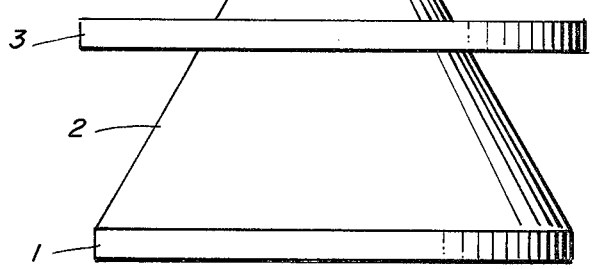
Figure 2:
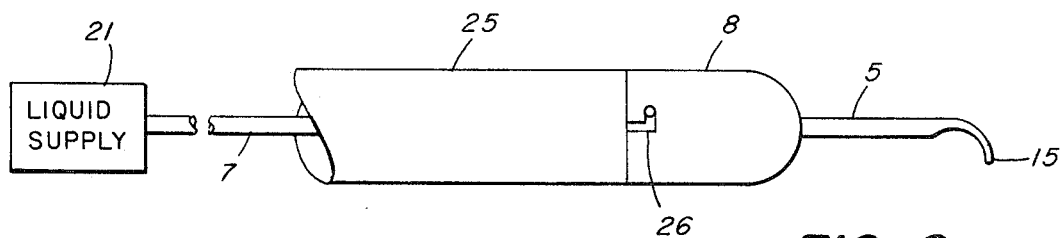
Figure 3:
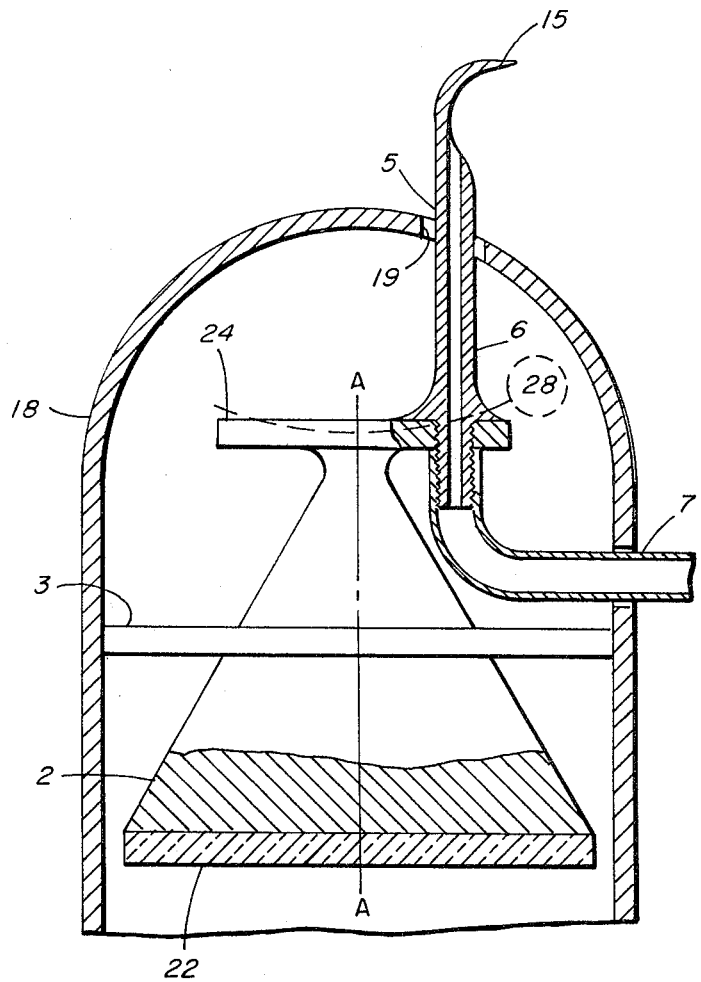

Apparatus for scaling teeth according to this invention comprises an elongated hollow tubular scaling tool having a working end formed for contacting the surface of a tooth to be cleaned of calculus, and a canal extending through the tool to the other end, through which water or other suitable liquid can be delivered to the working end during a scaling operation. Drive means is coupled to the other end of the tool for vibrating the working end at a frequency above the audible range. A second canal, or passage for a fluid, is provided through the drive means for introducing the liquid to the tool through the drive means. This combination has been found to be unusually effective and at the same time gentle for removing and flushing away calculus without damaging teeth or tissue surrounding them or causing pain to the patient. A description of presently preferred embodiments follows, with reference to the accompanying drawings. FIG. 1 is a partial longitudinal section through a scaler apparatus according to the invention;

FIG. 1A shows an assembly feature of FIG. 1;

FIG. 2 schematically illustrates a side view of the apparatus assembled to a handle; and FIG. 3 is a partial longitudinal section through a second version of a scaler according to the invention. FIGS. 1 and 3 show piezoelectric oscillation systems which are generally similar to those described in German Pat. No. 2,032,433 issued to Siemens AG Berlin and Munich on an application filed June 30, 1970 and first published Jan. 5, 1972. That patent is directed to the spraying of fluids in an atomizer. In the present invention the piezoelectric oscillating system is put to an entirely different use, which is not related to the spraying of liquids.

Referring to FIG. 1, a piezoelectric transducer element 1, made for example of barium titanate or other piezoelectric electromechanical converter material, is fixed at one side to the wide end of a cone-shaped mechanical coupling component 2. At the narrow end the coupling component is fixed to a working component 4. The acoustic length of the coupling component is such (e.g: one-half wave) that between the ends there is a nodal region, to which a mounting flange 3 is fixed. A tubular housing 8 surrounding the assembly 1-2-3-4 is fixed to the periphery of the mounting flange 3, and has a hole 9 in one end, for the passage of a scaling tool 5. A canal 10 passes through the coupling component 2, from a nipple 11 at the wide end to an internally-threaded socket 12 in the working component 4. The transducer element 1 has a central bore 13 through which the nipple 11 passes. A hose 7 or other suitable conduit is connected to the nipple for the purpose of bringing water or a dental treatment liquid to the canal 10. The socket 12 is open at its outer end, for receiving an externally-threaded connector 14 of the tool 5 (see FIG. 1A). A canal 6 extending axially through the tool couples end-to-end with the canal 10 when the tool 5 is assembled to the working component 4. The tool has a working end 15 that is shaped for scaling teeth in any known manner. The working end 15 is only one example of a useful shape for removing calculus from the surface of a tooth. In use, a fluid passing through the canals 10 and 6 is directed at the working end 15, where it is applied to the tooth being scaled, and to the surrounding tissue.

The housing 8 can be attached to a handle 25 by means of any suitable attachment, such as the bayonet mount 26, as is shown in FIG. 2. A supply of liquid 21 can be connected to the hose 7, the liquid supply being carried within or on the handle 25, or remote via an extended conduit, as may be desired by the user. A source 33 of appropriate electrical oscillations, shown in FIG. 1, may be connected via wires 31, 32 across the piezoelectric transducer element 11, for setting the piezoelectric element into oscillation at a desired frequency, all as is well known in the piezoelectric transducer art. These components 33, 32, 31 may be housed in the handle 25, in which case known means (not shown) to supply electric energy to the source of oscillations 33, together with suitable switching means, will also be included in a working device embodying the invention.

In FIG. 3, the piezoelectric element 22 is a disc without a central aperture and the working component 24 is disc-shaped, able to vibrate in a bending mode, illustrated by a dashed line 28 in a curved locus representing a dish-shaped posture the working component 24 can assume at a moment during a cycle of its oscillation in a bending mode which is known as the "umbrella" mode. The peripheral part of the working component moves back and forth parallel to the axis A—A of the coupling component 2, which already, according to the above-mentioned Ger. Patent No. 2,032,433, has concentrated the vibration from the piezoelectric transducer element 22 with increased amplitude in the center of the working component 24. The peripheral part of the working component may amplify still further the amplitude of vibration. An internally-threaded socket 42 is provided through the working component 24, near the periphery of the working component, for receiving the externally-threaded connector 14 of a tool 5. The connector 14 can extend through the working component for connection directly to a hose 7. Alternatively, a nipple (not shown)

like the nipple 11 in FIG. 1, can be fitted to the working component 24. The hose 7 is in this version of the invention taken out through a hole in the side of the housing 18, in which the hole 19 for passage of the tool 5 is off set from the axis A—A to accomodate the fact that the tool 5 is offset from the axis.

I claim:

1. Apparatus for scaling teeth comprising an elongated hollow tubular scaling tool having a working end formed for contacting the surface of a tooth to be cleaned of calculus, and a canal extending through the other end, means to introduce a liquid via said other end of the tool for delivery to the working end, and drive means consisting essentially of an electromechanical oscillator and a mechanical coupling component which vibrates in a longitudinal mode fixed together at a first end of said coupling component, a bending-mode vibrator fixed and supported in an intermediate region of its vibrational mode to the second end of said coupling component, said tool being coupled at said other end to said bending-mode vibrator in a peripheral second region thereof which is remote from said intermediate region, so as to impose elastic wave oscillations on said tool for vibrating the working end at a frequency above the audible frequency range.

2. Apparatus according to claim 1 in which said bending-mode vibrator is a disc which vibrates in an umbrella mode, and said coupling component is substantially of conical shape tapered from a larger transverse section at said first end to a smaller transverse section at said second end where it is fixed to said bending mode vibrator.

3. Apparatus according to claim 2 in which said coupling component has a mounting flange extending transversely from a region which is the locus of a node of the longitudinal vibration of said coupling component.

4. Apparatus according to claim 1 in which said bending-mode vibrator is a disc which vibrates in an umbrella mode, and said coupling component includes a tapered member which is tapered down from said electromechanical oscillator to said fixed support region of said bending mode vibrator.

5. Apparatus according to claim 1 in which said passage is through said second region of said bending mode member.

* * * * *